United States Patent
Jeon et al.

(10) Patent No.: US 8,916,354 B2
(45) Date of Patent: Dec. 23, 2014

(54) BLADDER CANCER DIAGNOSIS COMPOSITION CONTAINING APE1/REF-1 AND BLADDER CANCER DIAGNOSTIC KIT USING SAME

(75) Inventors: Byeong-Hwa Jeon, Daejeon (KR); Sung-A Choi, Daejeon (KR); Ju-Hyun Shin, Daejeon (KR)

(73) Assignee: The Industry & Academy Cooperation in Chungnam National University (IAC), Daejeon (KR)

( * ) Notice: Subject to any disclaimer, the term of this patent is extended or adjusted under 35 U.S.C. 154(b) by 0 days.

(21) Appl. No.: 13/990,798

(22) PCT Filed: Dec. 8, 2011

(86) PCT No.: PCT/KR2011/009446
§ 371 (c)(1),
(2), (4) Date: May 31, 2013

(87) PCT Pub. No.: WO2012/077983
PCT Pub. Date: Jun. 14, 2012

(65) Prior Publication Data
US 2013/0252255 A1     Sep. 26, 2013

(30) Foreign Application Priority Data
Dec. 8, 2010 (KR) .................. 10-2010-0125086

(51) Int. Cl.
*G01N 33/53* (2006.01)
*G01N 33/574* (2006.01)
*C12Q 1/34* (2006.01)

(52) U.S. Cl.
CPC ............ *C12Q 1/34* (2013.01); *G01N 33/57407* (2013.01); *G01N 2800/54* (2013.01); *G01N 2800/56* (2013.01)
USPC ........................................................ 435/7.1

(58) Field of Classification Search
None
See application file for complete search history.

(56) References Cited

PUBLICATIONS

Tell et al (Antioxidants and Redox Signaling, 2005, 7(3-4): 367-384).*
Sak et al (Clin Cancer Res, 2005, 11: 6205-6211).*
Kelley et al (Clin Cancer Res, 2001, 7: 824-830).*
Sak, S. C. et al. "APE1 and XRCC1 protein expression levels predicts cancer-specific survival . . . ", Clinical Cancer Research, Sep. 1, 2005, pp. 6205-6211, vol. 11(17).
Narter , K. F. et al. "Bladder cancer and polymorphisms of DNA repair genes . . . ", Anticancer Research, Apr. 2009, pp. 1389-1393, vol. 29(4).
Gangwar , R. et al. "Influence of XPD and APE1 DNA repair gene polymorphism on bladder cancer . . . ", Urology, Nov. 28, 2008, pp. 675-680, vol. 73(3).
Terry , P. D. et al. "APE1 genotype and risk of bladder cancer: evidence for effect . . . ", International Journal of Cancer, Jun. 15, 2006, pp. 3170-3073, vol. 118(12).
Gurusamy et al. "Redox activation of Ref-1 potentiates cell survival following . . . ", Free Radical Biology & Medicine, Apr. 29, 2007, pp. 397-407, vol. 43(3).
Xanthoudakis et al. "The redox and DNA-repair activities of Ref-1 are encoded by nonoverlapping domains", Proc. Natl. Acad. Sci. USA, Jan. 1994, pp. 23-27, vol. 91.
Tell et al. "The Intracellular Localization of APE1/Ref-1: More than a Passive . . . ", Antioxidants & Redox Signaling, Mar./Apr. 2005, pp. 367-384, vol. 7(3-4).
Ramana et al. "Activation of apurinicyapyrimidinic endonuclease in human cells by reactive oxygen . . . ", Proc. Natl. Acad. Sci. USA, Apr. 1998, pp. 5061-5066, vol. 95.
Jackson et al. "Analysis of nuclear transport signals in the human apurinic/apyrimidinic endonuclease", Nucleic Acids Research, Jun. 7, 2005, pp. 3303-3312, vol. 33, No. 10.
Qu et al. "Nitric oxide controls nuclear export of APE1/Ref-1 through S-nitrosation of Cysteines 93 and 3", Nucleic Acids Research, Apr. 1, 2007, pp. 2522-2532, vol. 35, No. 8.
Chattopadhyay et al. "Identification and characterization of mitochondrial abasic (AP) . . . ", Nucleic Acids Research, Apr. 14, 2006, pp. 2067-2076, vol. 34, No. 7.

\* cited by examiner

*Primary Examiner* — Sean Aeder
(74) *Attorney, Agent, or Firm* — Revolution IP, PLLC

(57) ABSTRACT

Provided are a bladder cancer diagnosis composition containing APE1/Ref-1, a bladder cancer diagnostic kit containing an antibody which specifically binds to the APE1/Ref-1, and a method of measuring APE1/Ref-1 concentration in biological samples through an antigen-antibody binding reaction using the antibody which specifically binds to the APE1/Ref-1. According to the invention, the APE1/Ref-1 protein concentration in serum of bladder cancer patients is significantly higher than in healthy subjects, and more particularly, it significantly increases in the serum of patients with stage 2 or later bladder cancer.

5 Claims, 3 Drawing Sheets

(A)

(B)

BLADDER CANCER DIAGNOSIS COMPOSITION CONTAINING APE1/REF-1 AND BLADDER CANCER DIAGNOSTIC KIT USING SAME

CROSS REFERENCE TO PRIOR APPLICATIONS

This application is a National Stage Application of PCT International Patent Application No. PCT/KR2011/009446 filed on Dec. 8, 2011, under 35 U.S.C. §371, which claims priority to Korean Patent Application No. 10-2010-0125086 filed on Dec. 8, 2010, which are all hereby incorporated by reference in their entirety.

TECHNICAL FIELD

The present invention relates to a bladder cancer diagnosis composition containing APE1/Ref-1, and a bladder cancer diagnostic kit using the same.

BACKGROUND ART

Bladder cancer is the most common cancer among genitourinary cancers, and its causes are relatively well known. It is known that the cancer develops from stimulation of the bladder wall when cigarette smoke or several chemicals (for example, leather dying paint, air pollutants, artificial sweeteners, and nitrates) are absorbed into the body and excreted in the urine.

A conventional bladder cancer test uses a method of finding abnormal cells in the urine but it has a low accuracy. Moreover, a cystoscopy test in which a catheter is inserted into the bladder and extracts suspected tissues is an invasive method and has relatively high accuracy.

In general, although a patient survival rate increases when bladder cancer is diagnosed at an early stage, it is difficult to diagnose bladder cancer at an early stage. A currently used bladder cancer diagnosis method uses a method in which a part of the body is incised, but it is difficult to diagnose bladder cancer at an early stage. Bladder cancer is classified as superficial or invasive cancer based on invasion of the bladder muscle layer, and about 30% of patients on average have the invasive bladder cancer at the time of the diagnosis. Accordingly, in order to increase a patient survival period, early diagnosis upon formation of a small range of lesions is best. Therefore, there is an urgent need to develop a diagnosis method that is more efficient than various existing bladder cancer diagnosis methods, that is, a method that can diagnose at an early stage and handle a large amount of samples, and a bladder cancer specific biomarker having a high sensitivity and specificity.

Meanwhile, APE1/Ref-1(apurinic/apyrimidinic endonuclease1/redox factor-1) is a multifunctional protein consisting of 318 amino acids including an oxidation-reduction region (redox region) and a DNA repair region. The protein is known to have a function of the APE1 recovering the damaged region when the DNA is damaged, and a redox function of the transcription factors, for example, AP-1 and NF-kB (Gurusamy, Malik et al. 2007). The transcription factor redox function of the APE1/Ref-1 facilitates transcription by reducing residue of the oxidized states of cysteine in the DNA bonding site of a plurality of transcription factors (Xanthoudakis, Miao et al. 1994; Tell, Damante et al. 2005).

The APE1/Ref-1 is present in all cells and tissues, and it is known that intracellular expression locations vary depending on the cells. The expression of the APE1/Ref-1 is regulated at the transcription and post-transcription levels. Reactive oxygen species (ROS) is a major cause of increased expression of the APE1/Ref-1. When macrophages and lymphocytes are treated with hydrogen peroxide and hypochlorous acid (HOCl), the expression of intracellular APE1/Ref-1 increases and this increase in the expression of the APE1/Ref-1 is considered as an adaptive response of the cells for protection against cell toxicity and oxidative stress (Ramana, Boldogh et al. 1998).

Various intracellular locations of the APE1/Ref-1 have been reported. Those diverse intracellular locations may be understood by analyzing protein sequences of the APE1/Ref-1. A nuclear localization signal (NLS) is present at an amino acid terminal side of the APE1/Ref-1 (Jackson, Theriot et al. 2005). APE1/Ref-1 can translocate from nucleus to cytoplasm in response to a nuclear export signal (NES) dependent on the S-nitrosation of cysteines 93 and 310 (Qu, Liu et al. 2007). Expression of the APE1/Ref-1 protein is also observed in mitochondria (Chattopadhyay, Wiederhold et al. 2006).

The APE1/Ref-1 protein created within cells may be isolated outside the cells. Inflammatory response and cell activation by endotoxin in the macrophage allow the APE1/Ref-1 to be isolated from the cells. Therefore, accurate measurement of the APE1/Ref-1 is important to understand potential functions of the APE1/Ref-1 in many biological processes, for example, heart cerebrovascular disease, inflammatory disease, and tumors.

However, it has not yet been reported that the APE1/Ref-1 protein acts as a bladder cancer diagnosis marker, and the resulting studies have not been made. Accordingly, there is an urgent need to develop a biomarker which can increase the patient survival rate by early diagnosis of bladder cancer from the blood at the time of health examinations with ease.

DISCLOSURE

Technical Problem

The inventors studied biomarkers which can rapidly, easily, and accurately diagnose bladder cancer at an early stage and observed that APE1/Ref-1 protein concentration in serum of bladder cancer patients was significantly higher than in healthy subjects, and more particularly, it significantly increased in the serum of patients with stage 2 or later bladder cancer, it increased in the serum of bladder cancer patients regardless of the number of recurrences, and the invention was thereby completed.

Technical Solution

The present invention provides a bladder cancer diagnosis composition containing APE 1/Ref-1.

Moreover, the invention provides a bladder cancer diagnostic kit containing an antibody which specifically binds to the APE1/Ref-1.

Furthermore, the invention provides a method of measuring APE1/Ref-1 concentration in biological samples through an antigen-antibody binding reaction using the antibody which specifically binds to the APE1/Ref-1, which is a marker of bladder cancer.

Advantageous Effects

According to the invention, the APE1/Ref-1 protein concentration in serum of bladder cancer patients was significantly higher than in healthy subjects, and more particularly, it significantly increased in the serum of patients with stage 2 or later bladder cancer. Moreover, when bladder cancer is recurrent, regardless of the number of recurrences, the APE1/Ref-1 protein concentration in the serum of bladder cancer patients is significantly higher than in bladder cancer patients at an early stage who did not experience recurrence. Therefore, since the APE1/Ref-1 protein of the invention may diagnose or predict bladder cancer at an early stage, it can be useful as a bladder cancer diagnosis marker.

MODES OF THE INVENTION

Figure 1:
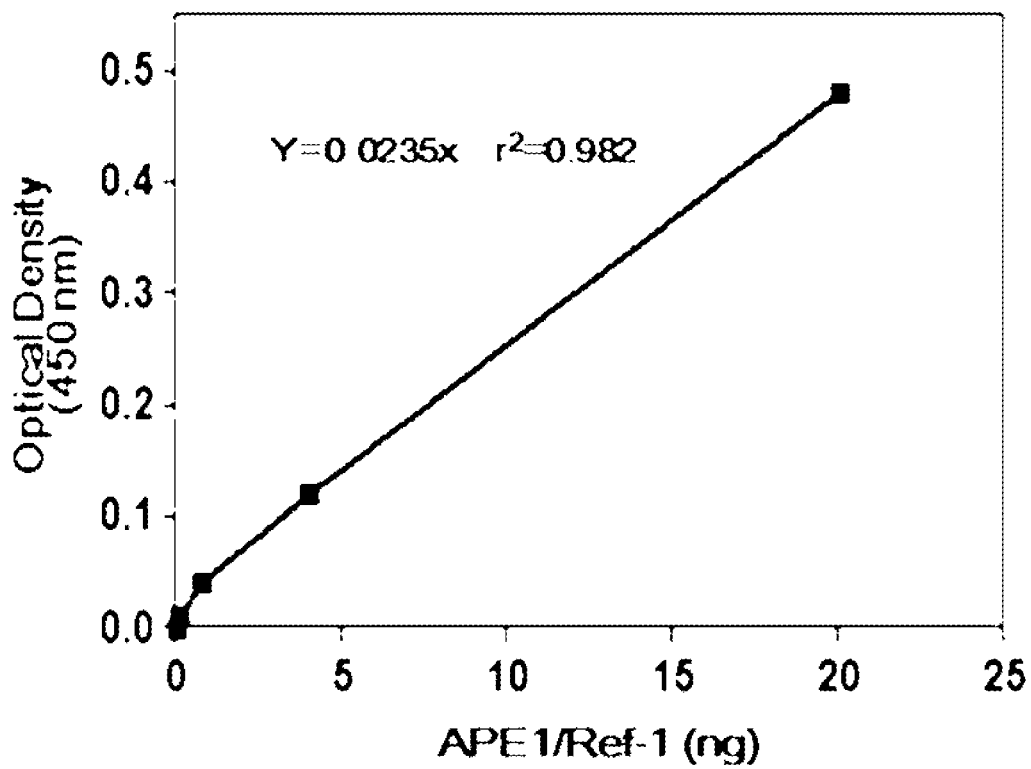
FIG. 1 illustrates an ELISA standard curve of APE1/Ref-1 protein.

The present invention provides a bladder cancer diagnosis composition containing APE1/Ref-1.

Moreover, the invention provides a bladder cancer diagnostic kit containing an antibody which specifically binds to the APE1/Ref-1.

Furthermore, the invention provides a method of measuring APE1/Ref-1 concentration in biological samples through an antigen-antibody binding reaction using the antibody which specifically binds to the APE1/Ref-1, which is a marker of bladder cancer.

Hereinafter, the invention will be described in detail.

According to the invention, the APE1/Ref-1 protein concentration in the serum of bladder cancer patients is 1.5 to 3.5 times higher than in healthy subjects. As the stages of bladder cancer increase, and more particularly with stage 2 or later bladder cancer, the APE1/Ref-1 protein concentration in the serum of bladder cancer patients significantly increases. Moreover, when bladder cancer is recurrent, regardless of the number of recurrences, the APE1/Ref-1 protein concentration in the serum of bladder cancer patients is significantly higher than in bladder cancer patients at an early stage who did not experience recurrence. Therefore, since the APE1/Ref-1 protein of the invention may diagnose or predict bladder cancer at an early stage, it can be useful as a bladder cancer diagnosis marker.

A bladder cancer diagnostic kit containing the antibody which specifically binds to the APE1/Ref-1 may be readily prepared by manufacturing methods commonly used in the related art using the APE1/Ref-1 protein.

The bladder cancer diagnostic kit may include, for example, the antibody which specifically binds to the APE1/Ref-1, secondary antibody conjugates conjugated with a marker which expresses colors by reactions with substrates, color-substrate solutions which are subjected to color reactions with the marker, washing solutions and enzyme reaction stop solutions.

As the marker of the secondary antibody conjugates, normal color agents performing color reactions are preferable, and fluorescein and dye, for example, horseradish peroxidase (HRP), alkaline phosphatase, coloid gold, FITC(poly L-lysine-fluorescein isothiocyanate), and RITC(rhodamine-B-isothiocyanate) may be used.

It is preferable that the color substrate solution is used according to the marker, and TMB (3,3',5,5'-tetramethyl bezidine), ABTS[2,2'-azino-bis(3-ethylbenzothiazoline-6-sulfonic acid)], and OPD(o-phenylenediamine) may be used. In this case, it is more preferable that the color substrate is provided in a state dissolved in the buffer solution (0.1M NaOAc and pH 5.5).

It is preferable that the washing solution includes a phosphate buffer solution, NaCl and tween 20. A buffer solution (PBST) including 0.02M phosphate buffer solution, 0.13M NaCl and 0.05% tween 20 is more preferable. The secondary antibody is reacted with the antigen-antibody complex after antigen-antibody binding reactions, and an appropriate amount of the washing solution is applied to fixtures and washes them three to six times. A sulfuric acid solution may be used as a reaction stop solution.

According to the invention, it is possible to diagnose or predict bladder cancer at an early stage by measuring the APE1/Ref-1 protein concentration in biological samples through the antigen-antibody binding reaction using the antibody which specifically binds to the APE1/Ref-1, which is a marker of bladder cancer. More specifically, the biological sample comes into contact with the capture antibody fixed in the fixtures, a remaining sample is separated from the fixed capture antibody, and then a fixed capture antibody-target molecule complex comes into contact with a detection antibody. Then, the APE1/Ref-1 protein concentration is measured in the biological samples using a detection method which can recognize the detection antibody. That is, APE1/Ref-1 concentrations in the serum of bladder cancer patients and healthy subjects are measured and compared. When the APE1/Ref-1 concentration in the serum of the bladder cancer patients is higher than in the healthy subjects, the bladder cancer patients are diagnosed with bladder cancer or predicted to have bladder cancer. Specifically, the APE1/Ref-1 protein concentration increases as the stage of bladder cancer increases, and more preferably, it significantly increases in the serum of patients with stage 2 or later bladder cancer.

The biological samples may include, for example, tissues, cells, whole blood, serum, plasma, saliva, sputum, and urine samples obtained from mammals, but the samples are not limited thereto. Before using, the samples may be pretreated with, for example, filtration, distillation, extraction, concentration, inactivation of interfering components, and addition of reagents.

Examples of the fixtures used for the antigen-antibody binding reaction may include a nitrocellulose membrane, a PVDF membrane (polyvinylidene difluoride membrane), a 96-well plate synthesized with a polyvinyl resin or a polystyrene resin, and a glass slide made of glass.

The antigen-antibody binding reaction may be performed using, for example, a conventional enzyme-linked immunosorbent assay (ELISA), a radioimmunoassay (RIA), a sandwich ELISA, a Western blot, an immunoprecipitation, an immunohistochemical staining, a flow cytometry, a fluorescence-activated cell sorting (FACS), an enzyme substrate color method, and an antigen-antibody agglutination.

The antibody of the invention may be an entire shape of antibody (hereinafter, referred to as "whole antibody") or a functional fragment thereof. The whole antibody may be a monomer or an oligomer in which two or more whole antibodies are bonded. The functional fragment of the antibody is an antibody which has heavy and light chain variable regions of the whole antibody, and substantially recognizes the same antigen binding region (epitope) as the whole antibody. The functional fragment of the antibody includes single chain variable region fragment (scFv), (scFv)2, Fab, Fab' and F(ab')2, but the invention is not limited thereto. The single chain variable region (scFv) means an antibody fragment in which the heavy chain variable region and the light chain variable region are connected through a linker peptide so as to form a single chain polypeptide.

The antibody may be transformed through binding a variety of molecules, for example, enzymes, fluorescent substances, radioactive substances, and proteins. The transformed antibody may be obtained by chemically transforming the antibody. These transformation methods are commonly used in the related art. The antibody may be obtained from a chimera antibody in which a variable region derived from a non-human antibody and a constant region derived from a human antibody are bonded, or may be obtained from a humanized antibody in which a complementarity-determining region derived from a non-human antibody and a frame work region (FR) and a constant region derived from a human antibody are bonded. These antibodies may be prepared using methods known in the related art.

Hereinafter, exemplary embodiments will be described in order to impart a sufficient understanding of the present invention. Embodiments described below are provided to facilitate understanding of the invention, but the scope of the invention is not limited to these embodiments.

Example 1

Measurement of APE1/Ref-1 Protein Concentration in Serum of Bladder Cancer Patient In order to measure APE1/Ref-1 protein concentration in the serum of bladder cancer patients, experiments described below were performed with the sandwich ELISA method.

1. Sample Preparation for ELISA

In order to measure an amount of the APE1/Ref-1 in the serum of bladder cancer patients and the healthy subjects, blood samples were collected from bladder cancer patients and healthy subjects with whole blood collection tubes containing an anticoagulant. About 10 ml of blood were collected from 51 bladder cancer patents and 56 healthy subjects who visited for health examinations. The collected blood samples were shacked and left at room temperature, then centrifuged for 10 min at 2500 rpm, and then a supernatant (that is, plasma) was separated. The separated supernatant was kept at a low temperature of 4° C. and used in an amount of 100 µL per sample when the sandwich ELISA was performed.

2. Determining Antibody and Standard Material for ELISA

As the capture antibody recognizing the APE1/Ref-1, an anti-APE1/Ref-1 polyclonal antibody was used (Abcam, ab64865). As the detection antibody recognizing the APE1/Ref-1 bonded to the capture antibody, an anti-APE1/Ref-1 monoclonal antibody (Abcam, ab194) was used. As a marker of the APE1/Ref-1, a recombinant human APE1/Ref-1-His, separated and purified of E-coli, was consecutively diluted by a factor of 5 and used (0-25 ng).

3. Sandwich ELISA Method

The capture antibody was diluted to a concentration of 200 ng/ml in the coating buffer solution (0.5M sodium bicarbonate buffer solution and pH 9.6) and was coated on the 96-well microliter plate for ELISA (BD Falcon 3072, Franklin, N.J.). The plate was coated at 4° C. overnight. In order to remove unbound APE1/Ref-1 polyclonal antibodies, the plate was washed three times with the washing solution (PBS, 0.05% Tween 20). After washing, the plate was blocked with the blocking solution (PBS, 5% bovine serum albumin, BSA) 250 µl for 1 hour at room temperature. 100 µl of serum samples of the bladder cancer patients and the healthy subjects were added to the 96-well plates, respectively, and reacted for 90 min at 37° C. The plate was washed five times with the washing solution. In order to identify a degree of APE1/Ref-1 bonded to the capture antibody, the detection antibody, the anti-APE1/Ref-1 monoclonal antibody, was diluted to a concentration of 200 ng/ml and reacted for 2 hours at room temperature. The plate was washed seven times with the washing solution. A HRP-linked anti-mouse IgG secondary antibody, which recognizes the detection antibody, was diluted to 1:5000 and added to the plate. The plate was reacted for 30 min at room temperature and washed five times with the washing solution. Tetramethyl benzidine (TMB), peroxidase substrates, and the peroxidase solution (BD555214, Franklin, N.J.) were added to the plate. When the color began to appear, the plate was reacted for 4 min at room temperature and regularly shacked. 5M $H_2SO_4$ was added as a reaction stop solution and the absorbance was measured at 450 nm.

4. Determining Standard Range of ELISA According to the Invention

The purified and separated recombinant human APE1/Ref-His was consecutively diluted in the range of 0-25 ng, thereby obtaining a standard curve indicating linearity as illustrated in Table 1 and FIG. 1.

Figure 2:
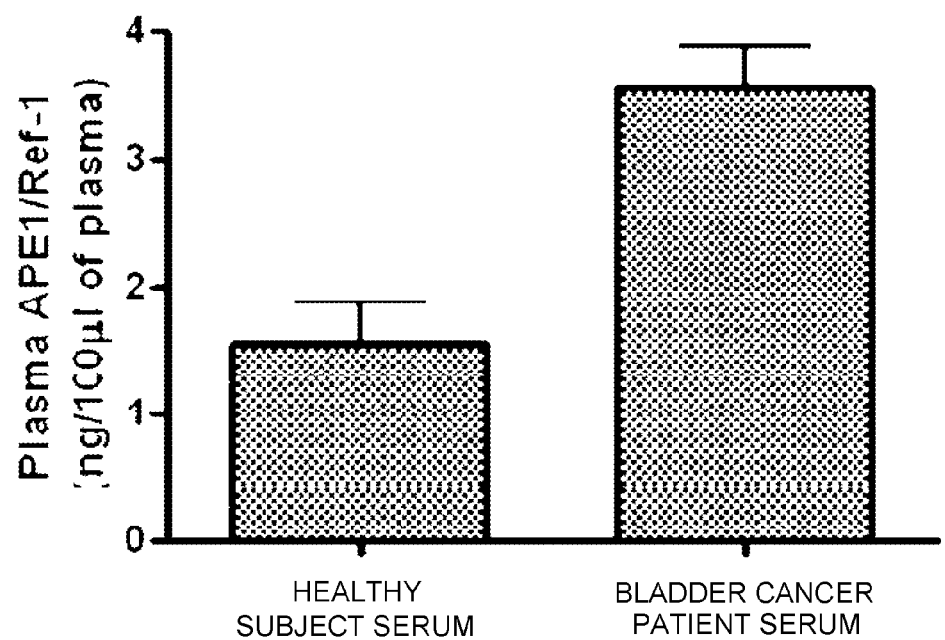
FIG. 2 is a comparison diagram illustrating the APE1/Ref-1 protein concentrations in serum of bladder cancer patients and healthy subjects measured with a sandwich ELISA method.
Figure 3:
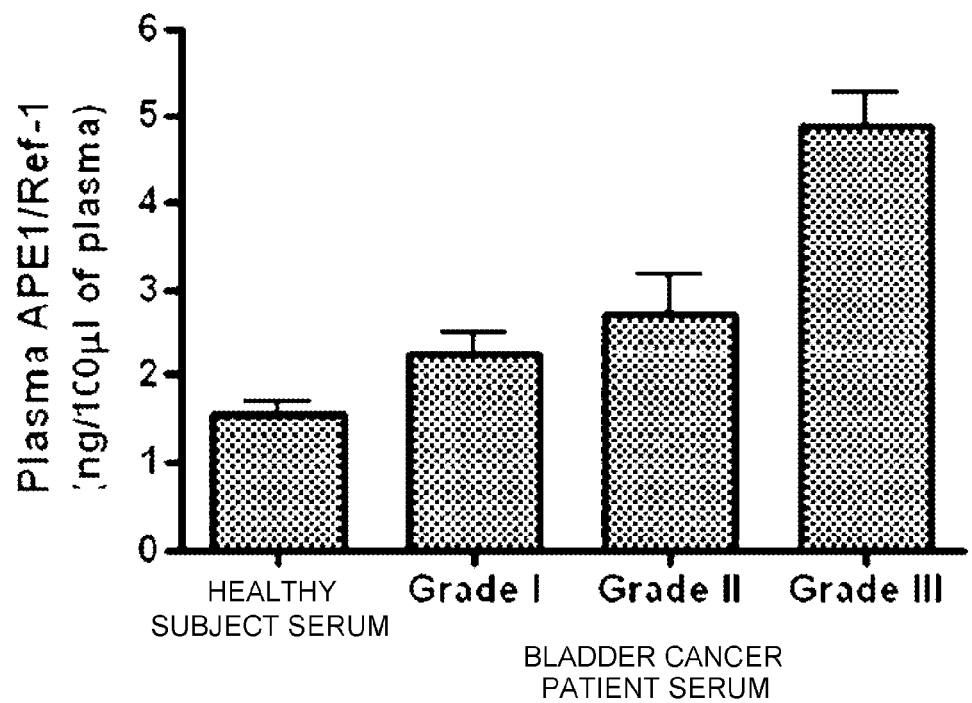
FIG. 3 illustrates the APE1/Ref-1 protein concentration in the serum of bladder cancer patients based on stage of bladder cancer.
Figure 4:
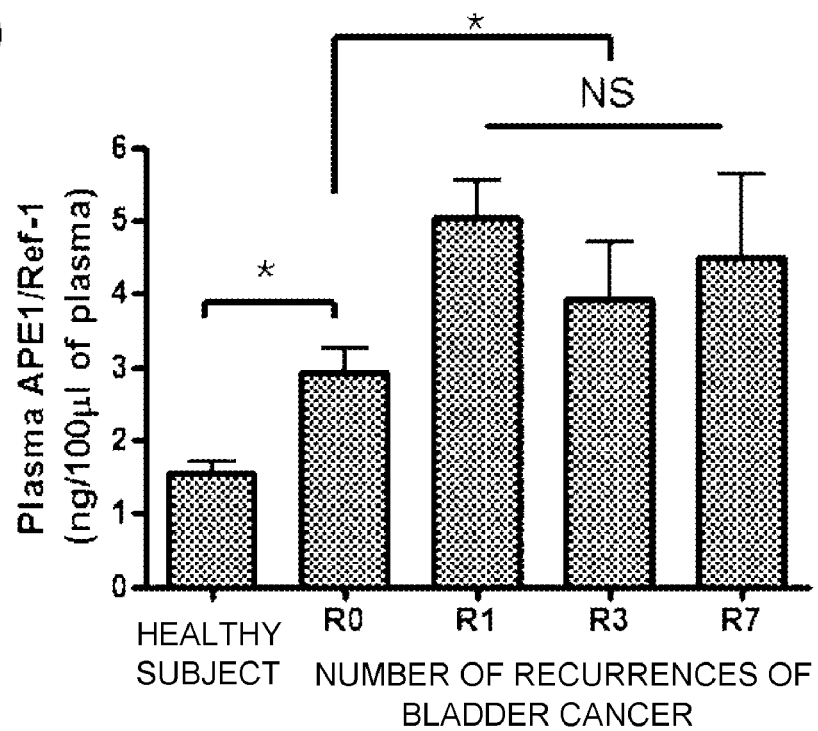
FIG. 4 is a diagram illustrating the APE1/Ref-1 protein concentration in the serum of bladder cancer patients based on a number of recurrences and a number of lesions of bladder cancer [(A) R0: no recurrence, R1: a number of recurrences is 1, R3: a number of recurrences is 3, R7: a number of recurrences is 7; (B) single: single lesion, multiple: multiple lesions].
Figure 4:
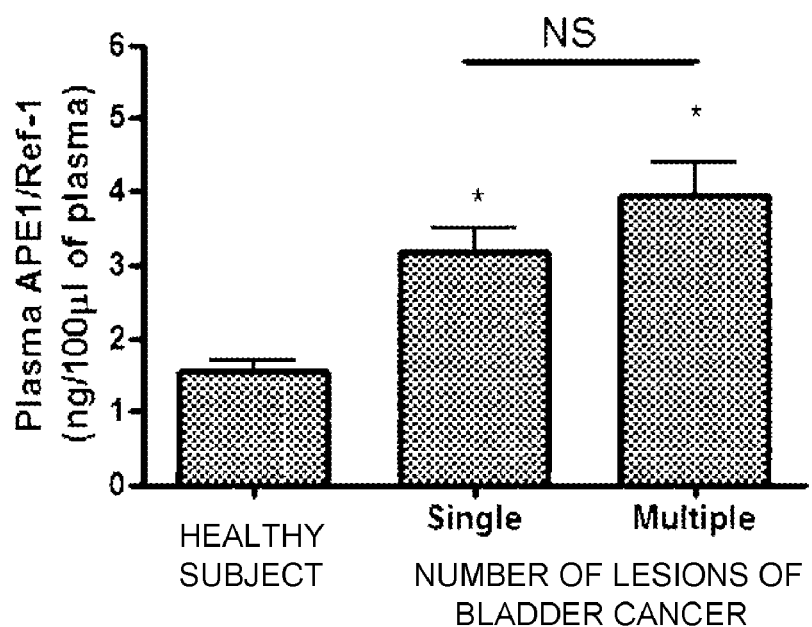

Table 2 and FIG. 2 illustrate comparison results of the APE1/Ref-1 protein concentrations in the serum of the bladder cancer patients and the healthy subjects measured with the sandwich ELISA method. FIG. 3 illustrates the APE1/Ref-1 protein concentration in the serum of the bladder cancer patients based on stage of bladder cancer. FIG. 4 illustrates the APE1/Ref-1 protein concentration in the serum of the bladder cancer patients based on a number of recurrences and a number of lesions of bladder cancer [(A) R0: no recurrence, R1: a number of recurrences is 1, R3: a number of recurrences is 3, R7: a number of recurrences is 7; (B) single: single lesion, multiple: multiple lesions].

TABLE 1

| APE1/Ref-His concentration (ng) | Absorbance | | | Zero standard subtracted |
|---|---|---|---|---|
| | OD1 | OD2 | Average value | |
| 0 | 0.0490 | 0.0480 | 0.0477 | 0.00 |
| 0.16 | 0.0530 | 0.0560 | 0.0543 | 0.01 |
| 0.8 | 0.0820 | 0.0810 | 0.0867 | 0.04 |
| 4 | 0.1940 | 0.2110 | 0.2083 | 0.12 |
| 20 | 0.5440 | 0.5110 | 0.5297 | 0.48 |

TABLE 2

| | APE1/Ref-1 protein concentration (ng/100 µl) in blood |
|---|---|
| Serum of healthy subjects | 1.547 ± 0.319 |
| Serum of bladder cancer patients | 3.548 ± 0.333 |

As illustrated in Table 2 and FIG. 2, the APE1/Ref-1 protein concentration in the serum of the bladder cancer patients was 1.5 to 3.5 times higher than in the healthy subjects.

As illustrated in FIG. 3, it was confirmed that, as the stages of bladder cancer increase, and more particularly with stage 2 or later bladder cancer, the APE1/Ref-1 protein concentration in the serum of the bladder cancer patients significantly increased.

As illustrated in FIG. 4, when bladder cancer was recurrent (R1, R3, and R7), regardless of the number of recurrences, the APE1/Ref-1 protein concentration in the serum of those bladder cancer patients was significantly higher than in the bladder cancer patients (R0) at an early stage who did not experience recurrence. However, the APE1/Ref-1 protein concentration in the serum of the bladder cancer patients did not increase in proportion to the number of recurrences of bladder cancer (FIG. 4A). Moreover, when there were multiple lesions of bladder cancer, the APE1/Ref-1 protein concentration showed a tendency to increase more than in the case of a single lesion, but there was no significant difference (FIG. 4B).

Therefore, since the APE1/Ref-1 protein of the invention may diagnose or predict bladder cancer at an early stage, it can be useful as a bladder cancer diagnosis marker.

The invention claimed is:

1. A method of diagnosing a bladder cancer, the method comprising;

binding a capture antibody to APE1/Ref-1 in blood, the blood being collected from a bladder cancer patient;

detecting the APE1/Ref-1 bound to the capture antibody using a detection antibody;

measuring a concentration of the APE1/Ref-1 in the blood using the detected APE1/Ref-1; and diagnosing a bladder cancer based on the measured APE1/Ref-1 concentration.

2. The method of claim 1, wherein the blood is whole blood.

3. The method of claim 1, wherein the capture antibody is an anti-APE1/Ref-1 polyclonal antibody.

4. The method of claim 1, wherein the detection antibody is an anti-APE1/Ref-1 monoclonal antibody.

5. The method of claim 1, wherein the collected blood is shacked and left at room temperature, then centrifuged for 10 min at 2500 rpm, and then plasma being separated thereof, the plasma being used in the binding step.

* * * * *